(12) United States Patent
Zhao et al.

(10) Patent No.: US 7,163,917 B2
(45) Date of Patent: Jan. 16, 2007

(54) SYNTHESIS METHOD OF ALANYLGLUTAMINE

(76) Inventors: Yufen Zhao, Department of Chemistry, Xiamen University, 422 Siming South Road, Xiamen, Fujian 361005 (CN); Guo Tang, Department of Chemistry, Xiamen University, 422 Siming South Road, Xiamen, Fujian 361005 (CN); Ning Zhou, Department of Chemistry, Xiamen University, 422 Siming South Road, Xiamen, Fujian 361005 (CN); Liming Hu, Department of Chemistry, Xiamen University, 422 Siming South Road, Xiamen, Fujian 361005 (CN); Yong Chen, Department of Chemistry, Xiamen University, 422 Siming South Road, Xiamen, Fujian 361005 (CN)

(*) Notice: Subject to any disclaimer, the term of this patent is extended or adjusted under 35 U.S.C. 154(b) by 0 days.

(21) Appl. No.: 10/518,940

(22) PCT Filed: May 30, 2003

(86) PCT No.: PCT/CN03/00417

§ 371 (c)(1),
(2), (4) Date: Jun. 8, 2005

(87) PCT Pub. No.: WO03/106481

PCT Pub. Date: Dec. 24, 2003

(65) Prior Publication Data

US 2005/0233977 A1   Oct. 20, 2005

(30) Foreign Application Priority Data

Jun. 17, 2002 (CN) ................................ 02 1 23369

(51) Int. Cl.
*A01N 37/18* (2006.01)

(52) U.S. Cl. ......................................................... 514/2
(58) Field of Classification Search ..................... 514/2
See application file for complete search history.

(56) References Cited

U.S. PATENT DOCUMENTS

| 4,898,930 A | 2/1990 | Kasafirek et al. |
| 5,032,675 A | 7/1991 | Kato et al. |

FOREIGN PATENT DOCUMENTS

CZ    SK 708-1998 A3    3/2000

OTHER PUBLICATIONS

A convenient method for the preparation of N-methoxyamides, J.Einhorn, C.Einhorn, J-L Luche, Synthetic communications, 1990, 20(8), 1105-1112.*
Reagents in Organic chemistry, R.Feiser, M.Feiser, vol. 1 p. 1247.*
Maziari et. al. convenient synthesis and diversification of Dehydroalanyl phosphinic peptide analogs., Organic Lettters., 3(5) 659—662, (2001).*

* cited by examiner

Primary Examiner—Bruce R. Campell
Assistant Examiner—Shyam Shirali
(74) Attorney, Agent, or Firm—Workman Nydegger

(57) ABSTRACT

A synthesis method of alanyl-glutamine includes the steps of: The N-terminal protected alanine reacts with triphenylphosphine and hexachloroethane in organic solvent to form active ester, the active ester reacts with glutamine in a solution mixture containing organic solvent and aqueous solution of inorganic base, the resultant mixture is acidified with inorganic acid, and then the N-terminal protecting group is removed. In this method, the raw materials are cheap, the synthesis technique is simple, no disposals of separation and purification are needed, the product is easy to be separated and purified, the toxicities of all the reagents used in the course of production are minimal, it is advantageous to environment protection.

15 Claims, No Drawings

SYNTHESIS METHOD OF ALANYLGLUTAMINE

THE FIELD OF THE INVENTION

The present invention relates to a synthesis method of amino acid containing dipeptide, especially a synthesis method of alanylglutamine.

RELEVANT TECHNOLOGY AND DETAILED DESCRIPTION OF PREFERRED EMBODIMENTS

Glutamine is the major content of amino acid in human body, the contents of glutamine in muscle protein and plasma protein are about 75% and 26% respectively.

Glutamine possesses important physiological action. Glutamine is the necessary precursor material of synthesizing nucleic acid of organisms, the regulator of synthesis and decomposition of protein, the carrier of amino nitrogen from peripheral tissue rotating to internal organs and the important matrix of ammonia excretion by the kidney. Glutamine is the important energy substance of epithelial cell of intestinal mucosa, renal tubule cell, macrophage and fibroblast. It plays important roles in various aspects, such as in maintaining intestinal function, promoting immunity function, maintaining alkali equilibrium within the body and elevating the adaptability of the organism to irritability.

Under the state of emergency and high catabolism such as clinical serious infection, combined fracture, major operation, extensive burn and the anaphase of malignant tumor etc., the necessity of glutamine greatly exceeds the capacity of synthesis of glutamine by the organism, it lowers the content of glutamine within the body, thus it renders the decreasing of nucleic acid and protein synthesis. If the traditional total phleboclysis nutrient solution (TPN) is adopted, it may cause the shrinkage of intestinal mucosa, elevating of thoroughfare of intestinal mucosa and bacteria transposal, even it will cause blood poisoning and multi-apparatus dispunction. It shows through a large number of experiments that the TPN supplemented with GLN displays remarkable effect in the preventing and recovery of many diseases. If a certain quantity of glutamine is added into the TPN to elevate the concentration of glutamine in tissues such as blood and muscle etc., it shows important effect in maintaining or recovering the function of intestinal mucosa. If the TPN supplemented with glutamine is transfused to the seriously infected patients, evident effects are shown in maintaining positive nitrogen equilibrium and promoting the expression of Gln synthetase of cells, reducing the decrease of concentrations of Gln and ribosome inside the myocyte.

In recent years, due to its important physiological and pharmacological actions, the application of glutamine in nutrition outside the intestines is attached importance generally to the public. As mentioned above, in irritability conditions such as various wounds (include accident wound, surgical wound and radiation wound), infections etc., the glutamine in blood and cells is lowered, and cannot be inverted by supplementing the medicament of amino acid (GLN not included) now available. Some important functions of cells, such as synthesis of protein, phagocytosis and multiplication of lymphocyte etc., are all necessary to depend on enough GLN. But as a result of it is low in solubility and unstable in solution, it produces toxic pyroglutamic acid and ammonia in the condition of heating to sterilize, so that no GLN is contained in commercial medicament of amino acid. At present, the applications of GLN are majorly through the following paths: (1) Use it up as soon as it is prepared; add GLN crystals to the solution of amino acid, and then filtered and sterilized, transfuse it within 8 hours. This process must be operated under aseptic condition and the labor is complicated and strenuous, so that the applicable scope is limited. (2) Synthesis of derivatives of GLN, such as acetylglutamine. It can be easily synthesized, it is stable at heating, and GLN may be formed within the body. But its utilizing ratio is low and 40% of the quantity absorbed is excreted from urea. (3) Application of the dipeptides of GLN At present, the dipeptides used in experimental investigation are majorly two kinds: glycylglutamine (L-glycyl-L-glutamine, L-Gly-L-Gln) and alanylglutamine (L-alanyl-L-glutamine, L-Ala-L-Gln). The experiments done in animals and human body show that within human body, these two kinds of dipeptide are quickly degraded into their composition amino acids, their half-life is short, only minor quantities of dipeptides are detected in blood, and only minor quantities of dipeptides are excreted from urea. These facts show that Gln dipeptide can be utilized effectively and they do not accumulate in blood, so that the possible pharmacological and physiological injures produced by dipeptides may be avoided. Experiments prove that, when healthy human body in a long period intravenous drips the L-Ala-L-Gln, no side effects and harmful reaction occur, and the normal kidney functions are not influenced. The solubility of L-Ala-L-Gln synthesized by chemical method after purification is 20 times of GLN monomer. It is stable in storage and at heating for sterilization. And when it enters the human body, it decomposes into GLN and exerts its action, it renders that the application of GLN in TPN is more convenient and practicable.

There are 4 kinds of synthesis method of alanylglutamine descibed as follows:

1. Firstly, protect the terminal amino group in GLN (glutamine), for example, to form carbobenzyloxy protecting glutamine (Cbz-Gln). The second step is to protect the acylamino group in Cbz-Gln to form Cbz-Gln $(OC_{13}H_9)$. The third step is to protect the carbonyl group of that in Cbz-Gln $(OC_{13}H_9)$ to form Cbz-Gln $(OC_{13}H_9)$OMe. The fourth step is passing hydrogen gas to form Gln $(OC_{13}H_9)$OMe. The fifth step is to add in Cbz-Ala. The sixth step is to activate the Cbz-Ala. The seventh step is Cbz-Ala combined with Gln $(OC_{13}H_9)$OMe to form peptide. The eighth step is to remove the methylester by saponification. The ninth step is to remove all the protections by acidification to form alanylglutamine. (Literature: Yasutsugu Shimomishi, Studies on the Synthesis of Peptides Containing Glutamine as the C-Terminal. Y. Bull. Chem. Soc. Jpn. 1962, 35, 1966) Steps of this reaction procedure is too many, the cost of the reagents is expensive, thus it has no practical value.

2. The following reaction is used: Under the action of dicyclohexyl carbodiimide (DCC), to let the carbobenzyloxy protecting alanine (Z-Ala) react with N-hydroxysuccinic imide (HOSu) at 20–25° C. for 5 hours, after filtering the dicyclohexylurea (DCU), proceed the synthesis in aqueous solution of sodium bicarbonate with non-protected Gln, the product is reduced by hydrogenation in methyl alcohol to remove the protective group, and then the alanylglutamine is obtained. (Literature: Katoh, T. Kurauchi, M. Eur, Pat. 311,057, 12 Apr. 1989) The reagents used in this method are expensive, it is difficult to remove the products of DCU after reaction, and the process of production is more complicated.

3. The following reaction is used: phosgene $(COCl_2)$ reacts with Ala to form mixed anhydride, then reacts with Gln in water, pH of the solution is maintained at 10.2, at last, remove protective group in acid solution, and then the alanylglutamine is obtained. (Literature: Frerst, P. Pfaendetr, P. Ger. Offen. DE 3206,784. 01 Sep. 1983) The reaction procedure of this method is less, but phosgene is a virulent gas, the reaction is hard to complete, and it is more harmful to human body.

4. Acyl chloride is formed by activating the chiral reagent chloropropionic acid with SOCl 2, and then reacts with Gln in aqueous solution of NaOH, pH of the solution is maintained at 10. The product is 2-chloropropionylglutamine, it reacts with liquid ammonia under a certain pressure, then the alanylglutamine is obtained. (Literature: Takahiro Sano, Toru Sugaya, Process Research and Development of 1-Alanul-1-glutamine, a Component of Parenteral Nutrition, Organic Process Research and Development, 2000, 4, 147–152). The raw material of this reaction is chiral reagent, it is higher in cost, in the synthesis procedure of acylchloride, reaction temperature is higher, and there are too many side reactions. So that when it is used in production, the production cost may be too expensive.

The object of this invention is to provide a synthesis method of alanylglutamine which is cheap in raw materials, simple in synthesis technique, low in production cost, high in productivity and advantageous to environment protection.

Procedure of the synthesis method of Alanylglutamine is provided below:

1) 10 mmol of N-terminal protected alanine (I), 10~30 mmol, preferably 15~20 mmol of triphenylphosphine and 10~30 mmol, preferably 15~20 mmol of hexachloroethane react in organic solvent (II) for 0.3~3 hours, preferably for 1.5~2 hours, at reaction temperature −5~30° C., preferably at 0~10° C., to form the active ester;

2) Let the reaction mixture containing the active ester as mentioned in step 1 to react with 10~30 mmol of glutamine in a mixed liquid containing organic solvent (III) and aqueous solution of inorganic base (IV), (due to there is organic solvent existed in step 1), the volume ratio of III and IV is 0~4, when the property of organic solvent (II) used in step 1 coincides with that of organic solvent (III), then no more organic solvent might be used in step 2, at this time, the volume ratio of III and IV is 0, preferably 0.5~2, the reaction temperature is −5~30° C., preferably 5~10° C., and pH of the solution is controlled at 8.5~13, preferably at 9.5~10.5. The most preferable procedure is that the step 2 is completed in stirring condition, that is, let the active ester obtained from step 1 reacts with 10~30 mmol of glutamine in a stirring liquid mixture of organic solvent (III) and aqueous solution of inorganic base (IV). While reacting, the condition of stirring and pH=9.5–10.5 must be maintained;

3) Acidify the solution to pH≦3.0, preferably 2.0–3.0 with inorganic acid (V); and then 4) Remove the N-terminal protecting group with deprotective reagent (VI), thus the alanylglutamine with a yield of 30%–65% is obtained, In which, (I) The N-terminal protected amino acid mainly is N—(O, O-dimethyl) phosphoalanine (DMP-L-Ala), N-(0,0-diethyl) phosphoalanine (DEP-L-Ala), N—(O,O-diisopropyl) phosphoalanine (DIPP-L-Ala), N—(O,O-di-n-butyl) phosphoalanine (DBP-Ala), carbobenzoxyalanine (Z-L-Ala), (para-carbomethoxy) carbobenzoxyalnine (MZ-L-Ala), tertbutylcarbonylalanine (Boc-L-Ala) 2-(dibiphenyl) isopropylcarbonylalanine (Bpoc-L-Ala), etc.

(II) The organic solvent is mainly dichloromethane, toluene, tetrahydrofuran, acetonitrile, 1,2-dichloroethane, etc.

(III) The organic solvent is mainly ethyl alcohol, ethyl acetate, petrolium ether, cyclohexane, toluene, dichloromethane, etc.

(IV) The inorganic base is mainly sodium hydroxide, potassium hydroxide, sodium bicarbonate, potassium bicarbonate, sodium carbonate, potassium carbonate, etc.

(V) The inorganic acid is mainly hydrochloric acid, sulfuric acid, nitric acid, phosphoric acid, etc.

(VI) The reagent used as deprotective group is mainly trifluoroacetic acid, hydrogen chloride/glacial acetic acid, hydrogen bromide/glacial acetic acid, methylsulfonic acid, hydrogenation reduction, hydrogenchloride/1,4-dioxane, hydrogen bromide/1,4-dioxane, etc.

In comparison with the synthesis methods now available, the major advantages of this invention are:

1) The raw materials are cheap;

2) The synthesis technique is simple, no separation of intermediate is needed, as the reaction is finished, it is easy to separate and purify the product;

3) The active ester forms in acidic medium, so the racemization of the product with the organic base is avoided;

4) Aqueous phase method is adopted in the second step of the reaction, the procedures of linking to and delete the protective group with glutamine amino acid is omitted, thus the route of synthesis is simplified and the reaction time is shortened;

5) Since aqueous phase method is used in the second step, inorganic base takes place of organic base, the production cost is reduced, and it is advantageous to environment protection;

6) As the reaction is finished, two products are produced, the one is alanylglutamine required, and the other is byproduct (triphenylphosphine oxide). The triphenylphosphine oxide is a non-volatile solid, which is easy to be recovered, and may be restored as raw material as well;

7) All the solvents used in the entire synthesis process may be recovered and reused easily.

In brief, the synthesis route of this method is simple, the raw materials are cheap and easy to be obtained, the synthesis technique is rational, it is advantageous to environment protection, and its production cost is low, therefore, it possesses excellent practical value.

With reference to following examples, further illustration of this invention is made.

EXAMPLE 1

Dissolve 20 mmol of hexachloroethane with 10 mmol of dichloromethane, drop it into a mixed system composed of 10 mmol of N—(O,O-dimethyl) phosphoalanine, 20 mmol of triphenylphosphine and 20 mmol of toluene. After reacting at 0° C. for 3 hours, drop the reaction mixture into a stirring mixture containing 25 mmol of glutamine, 20 ml of water and 60 ml of petroleum ether, regulate pH to 10 with 20 mmol of potassium hydroxide and then potassium bicarbonate successively, reaction temperature is 0° C., the reaction time after dropping is 1.5 hours, stirring and the condition of pH=10 are maintained during the course of the reaction, and then it is acidified to pH=2.5 with concentrated hydrochloric acid. The aqueous phase, after concentrated, reacts with methylsulfonic acid at room temperature for 20 hours. As the reaction is finished, add in 50 ml of ether, solids deposit, the product L-Ala-L-Gln with a yield of 65% is obtained by recrystallizing the solids with isopropanol-water. $[\alpha]_D$=10.55, C=2, m.p.=214–215.5.

EXAMPLE 2

Dissolve 20 mmol of hexachloroethane with 10 ml of dichlormethane, drop it into a mixed system composed of 10 mmol of N—(O,O-dimethyl) phosphoalanine, 20 mmol of triohenylphosphine and 20 ml of toluene. After reacting at 0° C. for 3 hours, drop it into a liquid mixture containing 25 mmol of glutamine, 20 ml of water and 60 ml of petrolium ether. While reacting, regulate pH to 10 with 20 mmol of potassium hydroxide and then with potassium carbonate successively, the reaction temperature is 0° C. the reaction time after dropping is 1.5 hours. Then acidify it to regulate pH=2.5 with concentrated hydrochloric acid. The aqueous phase, after concentrated, reacts with methylsulfonic acid at room temperature for 20 hours. As the reaction is finished, add in 50 ml of ether, solids deposit, the product L-Ala-L-Gln is obtained with a yield of 45% by recrystallizing the solids with isopropanol-water.

EXAMPLE 3

Dissolve 20 mmol of hexachloroethane with 10 ml of dichlormethane, drop it into a mixed system composed of 10 mmol of N—(O,O-dimethyl) phosphoalanine, 20 mmol of triphenylphospine and 20 ml of toluene. After reacting at 0° C. for 3 hours, drop it into a liquid mixture containing 25 mmol of glutamine, 20 ml of water and 60 ml of petroleum ether. While reacting, regulate pH to 10 with 20 mmol of potassium hydroxide and then with potassium carbonate successively, the reaction temperature is 0° C. the reaction time after dropping is 1.5 hours. Then acidify it to regulate pH=2.5 with concentrated hydrochloric acid. The aqueous phase, after concentrated, reacts with methylsulfonic acid at room temperature for 20 hours. As the reaction is finished, add in 50 ml of ether, solids deposit, the product L-Ala-LGln is obtained with a yield of 45% by recrystallizing the solids with isopropanol-water.

EXAMPLE 4

In a round bottom flask, add in 10 mmol of N—(O,O-dimethyl) phosphoalanine, 20 mmol of triphenylphosphine and 30 mmol of hexachloroethane respectively, and then add in 20 ml of toluene. After reacting at 5° C. for 1 hour, add it into a liquid mixture containing 10 mmol of glutamine, 20 ml of water and 5 ml of ethanol. While reacting, regulate pH to 9.5 with sodium carbonate, the reaction temperature is 5° C., the reaction time is 10 min. And then regulate pH to 1.0 by acidifying it with phosphoric acid. The aqueous phase, after concentrated, reacts with trifluoroacetic acid at room temperature for 15 hours. As the reaction is finished, add in 50 ml of ether, solids deposit, the product L-Ala-L-Gln with a yield of 40% is obtained by recrystallizing the solids with methanol-water.

EXAMPLE 5

Dissolve 20 mmol of triphenylphosphine with 10 ml of tetrahydrofuran, drop it into a mixed system composed of 10 mmol of N—(O,O-diethyl) phosphoalanine, 30 mmol of hexachloroethane and 10 ml of tetrahydrofuran. After reacting at −5° C. for 2 hours, add it into a liquid mixture containing 10 mmol of glutamine, 20 ml of water and 20 ml of ethanol. While reacting, regulate pH to 9.5 with 10 mmol of sodium hydroxide and then with sodium bicarbonate successively, the reaction temperature is −5° C., the reaction time after dropping is 2 hours. And then acidify it to regulate pH=3 with concentrated hydrochloric acid. The aqueous phase, after concentrated, reacts with saturated hydrogen chloride/glacial acetic acid at room temperature for 5 hours. As the reaction is finished, adding 50 ml of ether, solids deposit, the product L-Ala-L-Gln is obtained with a yield of 35% by recrystallizing the solids with ethanol-water.

EXAMPLE 6

Dissolve 30 mmol of hexaethane with 20 ml of dichloromethane, drop it into a mixed system composed of 10 mmol of N—(O,O-diethyl) phosphoalanine, 30 mmol of triphenylphosphine and 10 ml of dichloromethane. After reacting at 0° C. for 40 min., drop it into a liquid mixture containing 30 mmol of glutamine, 20 ml of water and 10 ml of cyclohexane. While reacting, regulate pH to 13 with potassium hydroxide, the reaction temperature is 20° C., the reaction time after dropping is 30 min. And then acidify it to regulate pH=1.5 with dilute nitric acid. The aqueous phase, after concentrated, react with trifluoroacetic acid at room temperature for 10 hours. As the reaction is finished, add in 50 ml of ether, solids deposit, the product L-Ala-L-Gln is obtained with a yield of 60% by recrystallizing the solids with 1,4-dioxane-water.

EXAMPLE 7

In a round bottom flask, add in 10 mmol of N—(O,O-diethyl) phosphoalanine, 10 mmol of triphenylphosphine and 15 mmol of hexachloroethane respectively, and then add in 20 ml of acetonitrile. After reacting at 15° C. for 2.5 hour, drop it into a liquid mixture composed of 30 mmol of glutamine, 20 ml of water and 30 ml of toluene. While reacting, regulate pH to 8.5 with sodium carbonate, the reaction temperature is 30° C., the reaction time after dropping is 1 hour. And then acidify it to regulate pH=2 with dilute sulfuric acid. The aqueous phase, after concentrated, reacts with saturated hydrogen bromide/1,4-dioxane at room temperature for 5 hours. As the reaction is finished, add in 50 ml of ether, solids deposit, the product L-Ala-L-Gln is obtained with a yield of 40% by recrystallizing the solids with tetrahydrofuran-water.

EXAMPLE 8

In a round bottom flask, add in 10 mmol of N—(O,O-diisopropyl) phosphoalanine, triphenylphosphine and hexachloroethane respectively, and then 20 ml of tetrahydrofuran. After reacting at 30° C. for 2 hours, drop it into a liquid mixture containing 15 mmol of glutamine, 20 ml of water and 10 ml of ethanol. While reacting, regulate pH to 10.5 with sodium hydroxide, the reaction temperature is −5° C., the reaction time after dropping is 2 hours. And then regulate pH to 3.0 with concentrated hydrochloric acid. The aqueous phase, after concentrated, reacts with saturated hydrogen chloride/glacial acetic acid at room temperature for 2 hours. As the reaction is finished, add in 50 ml of ether, solids deposit, the product L-Ala-L-Gln with a yield of 60% is obtained by recryatallizing the solids with ethanol-water.

EXAMPLE 9

Dissolve 15 mmol of triphenylphosphine with 20 ml of dichloromethane, drop it into a mixed system composed of 10 mmol of N—(O,O-diisopropyl) phosphoalanine, 20 mmol of hexachloroethane and 10 mmol of dichloromethane. After reacting at 10° C. for 3 hours, add it into a liquid mixture containing 10 mmol of glutamine, 20 ml of water and 20 ml of ethylacetate. While reacting, regulate pH to 9 with 10 mmol of sodium hydroxide and then with sodium carbonate successively, the reaction temperature is 10° C., and the reaction time after dropping is 1 hour. And then acidify it to regulate pH=2.0 with dilute sulfuric acid. The aqueous phase, after concentrated, reacts with 20% hydrogen bromide/glacial acetic acid at room temperature for 5 hours. As the reaction is finished, add in 50 ml of ether, solids deposit, the product L-Ala-L-Gln is obtained with a yield of 45% by recrystallizing the solids with methyl alcohol-water.

EXAMPLE 10

Dissolve 15 mmol of hexachloroethane with 10 ml of 1,2-dichloroethane, add it into a mixed system composed of 10 mmol of N—(O,O-diisopropyl) phosphoalanine, 15 mmol of triphenylphosphine, and 10 ml of 1,2-dichloroethane. After reacting at 20° C. for 1.5 hours, drop it into 20 ml of water containing 20 mmol of glutamine. While reacting, regulate pH to 13 with potassium hydroxide, the reaction temperature is 10° C., the reaction time after dropping is 2 hours. And then regulate pH to 1.5 by acidifying it with dilute nitric acid. The Aqueous phase, after concentrated, reacts with trifluoroacetic acid at room temperature for 10 hours. As the reaction is finished, add in 50 ml of ether, solids deposit, the product L-Ala-L-Gln with a yield of 52% is obtained by recrystallizing the solids with isopropanol-water.

EXAMPLE 11

In a round bottom flask, add in 10 mmol of tert-butylcarbonylalanine (Boc-Ala), 15 mmol of triphenyl phosphine and 20 mmol of hexachloroethane, and then add in 20 ml of 1,2-dichloroethane. After reacting at 10° C. for 20 min, drop it into a liquid mixture containing 30 mmol glutamine, 20 ml of water and 20 ml of cyclohexane. While reacting, regulate pH to 11 with potassium hydroxide, the reaction temperature is 20° C., the reaction time after dropping is 30 min. And then acidify it to regulate pH=1.5 with dilute nitric acid. The aqueous phase, after concentrated, reacts with trifluoroacetic acid at room temperature for 15 hours. As the reaction is finished, add in 50 ml of ether, solids deposit, the product L-Ala-L-Gln with a yield of 40% is obtained by recrystallizing the solids with tetrahydrofuran-water.

EXAMPLE 12

Dissolve 10 mmol of triphenylphosphine with 10 ml of toluene, drop it into a mixed system composed of 10 mmol of tert-butylcarbonylalanine (Boc-Ala), 10 mmol of hexachloroethane and 20 ml of toluene. After reacting at 5° C. for 2 hours, drop it into a liquid mixture containing 15 mmol of glutamine, 20 ml of water and 60 ml of petrolium ether. While reacting, regulate pH to 12 with sodium hydroxide, the reaction temperature is 10° C., the reaction time after dropping is 1.5 hours. And then acidify it to regulate pH=1.5 with dilute sulfuric acid. The aqueous phase, after concentrated, reacts with hydrogen chloride/1,4-dioxane at room temperature for 5 hours. As the reaction is finished, add in 50 ml of ether, solids deposit, the product L-Ala-L-Gln with a yield of 52% is obtained by recrystallizing the solids with 1,4-dioxane-water.

EXAMPLE 13

Dissolve 20 mmol of hexachloroethane with 10 ml of tetrahydrofuran, drop it into a mixed system composed of 10 mmol of tert-butylcarbonylalnine (Boc-Ala), 20 mmol of triphenylphosphine and 20 ml of tetrahydrofuran. After reacting at 0° C. for 1.5 hours, drop it into a liquid mixture containing 20 mmol of glutamine, 20 ml of water and 15 ml of dichloromethane. While reacting, regulate pH to 10 with 20 mmol of potassium hydroxide and then with sodium carbonate successively, the reaction temperature is 8° C., the reaction time after dropping is 2 hours. And then acidify it to regulate pH=2.0 with concentrated hydrochloric acid. The aqueous phase, after concentrated, reacts with methylsulfonic acid at room temperature for 20 hours. As the reaction is finished, add in 50 ml of ether, solids deposit, the product L-Ala-L-Gln with a yield of 45% is obtained by recrystallizing the solids with methanol-water.

EXAMPLE 14

In a round bottom flask, add in 10 mmol each of carbobenzoxy-alanine (Z-Ala), triphenylphosphine and hexachloroethane respectively, and then 30 ml of toluene. After reacting at 0° C. for 3 h., drop it into a liquid mixture containing 25 mmol of glutamine and 20 ml of water. While reacting, regulate pH to 12 with sodium hydroxide, the reaction temperature is 15° C., the reaction time after dropping is 1.5 hours. And then acidify it to pH=2.5 with dilute hydrochloric acid. The aqueous phase, after concentrated, reacts with hydrogen gas in methanol at room temperature for 15 hours. The product L-Ala-L-Gln with a yield of 48% is obtained.

EXAMPLE 15

Dissolve 15 mmol of triphenylphosphine with 10 ml of tetrahydrofuran, drop it into a mixed system composed of 10 mmol of carbobenzoxy-alanine (Z-Ala), 20 mmol of hexachloroethane and 10 ml of tetrahydrofuran. After reacting at 0° C. for 1.5 hours, drop it into a liquid mixture containing 18 mmol of glutamine, 20 ml of water and 40 ml of dichloromethane. While reacting, regulate pH to 13 with potassium hydroxide, the reaction temperature is 0° C., the reaction time after dropping is 2 hours. And then acidify it to regulate pH=2.0 with dilute sulfuric acid. The aqueous phase, after concentrated, reacts with hydrogen in methanol at room temperature for 15 hours. The product L-Ala-L-Gln with a yield of 65% is obtained.

EXAMPLE 16

Dissolve 30 mmol of hexachloroethane with 10 ml of acetonitrile, drop it into a mixed system composed of 10 mmol of carbobenzoxy alanine (Z-Ala), 20 ml of triphenylphosphine and 10 ml of acetonitrile. After reacting at 5° C. for 1.0 h., drop it into 20 ml of water containing 10 mmol of glutamine. While reacting, regulate pH to 10 with 20 mmol of sodium hydroxide and then potassium carbonate successively, the reaction temperature is 5° C., and the reaction time after dropping is 2 hours. And then acidify it to regulate pH to 3.0 with concentrated hydrochloric acid. The aqueous phase, after concentrated, reacts with trifluoroacetic acid at room temperature for 40 hours. After the reaction is finished, add in 50 ml of ether, solids deposit, the product L-Ala-L-Gln is obtained with a yield of 45% by recrystallizing the solids with 1,4-dioxane-water.

What is claimed is:

1. A method of synthesizing alanylglutamine, comprising the steps of:
   1) form active ester by the reaction of 10 mmol N-terminal protected alanine, 10 to 30 mmol of triphenylphosphine and 10 to 30 mmol of hexachloroethane, in organic solvent for 20 minutes to 3 hours, and reaction temperature is −5 to 30° C.;
   2) react the active ester obtained from step 1) with 10 to 30 mmol of glutamine to form N-terminal protected alanylglutamine, in a liqiuid mixture made by organic solvent and aqueous solution of inorganic base, wherein the volume ratio of organic solvent and aqueous solution of inorganic base is 0–4, reaction temperature is −5 to 30° C. and the pH is controlled at 8.5 to 13;
   3) acidify the reaction mixture of step 2) with inorganic acid to pH <3.0; and
   4) remove the N-terminal protecting group to obtain alanylglutamine.

2. The method of synthesizing alanylglutamine according to claim 1, wherein:
   1) forms an active ester by the reaction of 10 mmol of N-terminal protected alanine, 15 to 20 mmol of triphenylphosphine and 15 to 20 mmol of hexachloroethane in organic solvent for 1.5 to 2 hours and the reaction temperature is 0 to −10 ° C.;
   2) react the active ester obtained from step 1) with 15 to 20 mmol of glutamine to form N-terminal protected alanylglutamine, in a liquid mixture made by mixing organic solvent and aqueous solution of inorganic base, wherein the volume ratio of organic solvent and aqueous solution of inorganic base is 0.5 to 2, reaction temperature is 5 to 10° C., and pH is controlled at 9.5 to 10.5 ; and
   3) acidify the reaction mixture of step 2) to a pH of 2.0 to 3.0.

3. The synthesis method of alanylglutamine according to claim 1, wherein N-terminal protected alanine is N—(O,O-dimethyl) phosphoalanine (DMP-L-Ala), N—(O,O-diethyl) phosphoalanine (DEP-L-Ala), N—(O,O-diisopropyl) phosphoalanine (DIPP-L-Ala), N—(O,O-di-n-butyl) phosphoalanine (DBP-Ala), carbobenzoxyalanine (Z-L-Ala), (para-carbomethoxy) carbobenzoxyalanine (MZ-L-Ala), tert-butylcarbonylalanine (Boc-L-Ala), or 2-(dibiphenyl) isopropylcarbonylalanine (Bpoc-L-Ala).

4. The synthesis method of alanylglutamine according to claim 1, wherein: wherein the organic solvent used in step 1) is selected from the group consisted from the group consisting of dichloromethane, toluene, tetrahydrofuran, acetonitrile, and 1,2-dichloroethane.

5. The synthesis method of alanylglutamine according to claim 2, wherein: wherein the organic solvent used in step 1) is selected from the group consisted from the group consisting of dichloromethane, toluene, tetrahydrofuran, acetonitrile, and 1,2-dichloroethane.

6. The synthesis method of alanylglutamine according to claim 1, wherein the organic solvent used in step 2) is selected from the group consisting of ethanol, ethyl acetate, petroleum ether, cyclohexane, toluene and dichloromethane.

7. The synthesis method of alanylglutamine according to claim 2, wherein the organic solvent used in step 2) is selected from the group consisting of ethanol, ethyl acetate, petroleum ether, cyclohexane, toluene and dichloromethane.

8. The synthesis method of alanylglutamine according to claim 1, wherein the inorganic base used in step 2) is selected from the group consisting of sodium hydroxide, potassium hydroxide, sodium bicarbonate, potassium bicarbonate, sodium carbonate and potassium carbonate.

9. The synthesis method of alanylglutamine according to claim 2, wherein the inorganic base used in step 2) is selected from the group consisting of sodium hydroxide, potassium hydroxide, sodium bicarbonate, potassium bicarbonate, sodium carbonate and potassium carbonate.

10. The synthesis method of alanylglutamine according to claim 1, wherein the inorganic acid used in step 3) is selected from the group consisting of hydrochloric acid, sulfuric acid, nitric acid and phosphoric acid.

11. The synthesis method of alanylglutamine according to claim 2, wherein the inorganic acid used in step 3) is selected from the group consisting of hydrochloric acid, sulfuric acid, nitric acid and phosphoric acid.

12. The synthesis method of alanylglutamine according to claim 1, wherein the N-terminal protecting group is removed by at least one of trifluoroacetic acid, hydrogen chloride/glacial acetic acid, hydrogen bromide/glacial acetic acid, methyl sulfonic acid, hydrogenation reduction, hydrogen chloride/1,4-dioxane, or hydrogen bromide/1,4-dioxane.

13. The synthesis method of alanylglutamine according to claim 2, wherein the N-terminal protecting group is removed by at least one of trifluoroacetic acid, hydrogen chloride/glacial acetic acid, hydrogen bromide/glacial acetic acid, methyl sulfonic acid, hydrogenation reduction, hydrogen chloride/1,4-dioxane, or hydrogen bromide/1,4-dioxane.

14. The synthesis method of alanylglutamine according to claim 1, wherein step 2) is accomplished as follows: the active ester obtained from step 1) reacts with glutamine in a stirring liquid mixture containing organic solvent and aqueous solution of inorganic base, and stirring and the condition of 9.5 to 10.5 must be maintained in the course of reaction.

15. The synthesis method of alanylglutamine according to claim 2, wherein step 2) is accomplished as follows: the active ester obtained from step 1) reacts with glutamine in a stirring liquid mixture containing organic solvent and aqueous solution of inorganic base, and stirring and the condition of 9.5 to 10.5 must be maintained in the course of reaction.

* * * * *